(12) United States Patent
Kitamura (10) Patent No.: US 8,319,090 B2
(45) Date of Patent: Nov. 27, 2012

(54) ORGANIC PHOTOELECTRIC CONVERSION MATERIAL AND ORGANIC THIN-FILM PHOTOELECTRIC CONVERSION DEVICE

(75) Inventor: Tetsu Kitamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 608 days.

(21) Appl. No.: 12/474,937

(22) Filed: May 29, 2009

(65) Prior Publication Data
US 2009/0293956 A1    Dec. 3, 2009

(30) Foreign Application Priority Data

May 30, 2008   (JP) ................................ 2008-143256

(51) Int. Cl.
*H01L 31/042*   (2006.01)
*H01L 31/00*    (2006.01)
(52) U.S. Cl. .................. 136/244; 136/256; 136/263
(58) Field of Classification Search .................. 136/263, 136/256, 244; 429/111, 328
See application file for complete search history.

(56) References Cited

U.S. PATENT DOCUMENTS 6,376,765 B1 * 4/2002 Wariishi et al. ............... 136/263

FOREIGN PATENT DOCUMENTS

| JP | 2001-117201 A | 4/2001 |
| JP | 2003-234460 A | 8/2003 |
| JP | 2003-332551 A | 11/2003 |
| JP | 2005-268609 A | 9/2005 |

OTHER PUBLICATIONS

Ysaui, Syntheses and Some Properties of Infrared-Absorbing Croconium and Related Dyes Dyes and Pigments, 10, 13-22(1988).*

Jana Zaumseil et al., "Electron and Ambipolar Transport in Organic Field-Effect Transistors," Chem. Rev., 2007, pp. 1296-1323, vol. 107.
Abhijit Basu Mallik et al., "Organic Field-Effect Transistors", CRC Press., (2007), pp. 159-229.
Shigeo Yasui et al., "Syntheses and Some Properties of Infrared-Absorbing Croconium and Related Dyes," Dyes and Pigments, 1988, pp. 13-22, vol. 10.
Paul A. Lane et al., "Organic Photovoltaics", Taylor & Francis, 2005,pp. 49-104.
Serap Gunes et al., "Conjugated Polymer-Based Organic Solar Cells", Chem. Rev., 2007, pp. 1324-1338, vol. 107.

* cited by examiner

*Primary Examiner* — Ling Choi
*Assistant Examiner* — Monique Peets
(74) *Attorney, Agent, or Firm* — Sughrue Mion, PLLC (57) ABSTRACT

An organic photoelectric conversion material for use in an organic thin-film photoelectric conversion device, containing a compound represented by formula 1; and an organic thin-film photoelectric conversion device having a photoelectric conversion layer which containing the organic photoelectric conversion material:

Formula 1

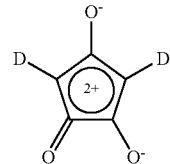

wherein D represents an electron-donating aromatic substituent whose bonding site atom is a $sp^2$ carbon atom; and a plurality of D may be the same or different from each other.

13 Claims, 2 Drawing Sheets

ORGANIC PHOTOELECTRIC CONVERSION MATERIAL AND ORGANIC THIN-FILM PHOTOELECTRIC CONVERSION DEVICE

FIELD OF THE INVENTION

The present invention relates to an organic photoelectric conversion material containing a compound having a particular chemical structure, and to a high-performance organic thin-film photoelectric conversion device using the organic photoelectric conversion material.

BACKGROUND OF THE INVENTION

With the arrival of a ubiquitous information society, an information terminal is demanded to transfer information anytime, anywhere. For such a terminal, flexible, lightweight, and inexpensive electronic devices are required, but the conventional devices using inorganic semiconductor materials such as silicon does not sufficiently meet the requirement. Accordingly, in recent years, electronic devices using organic semiconductor materials as semiconductors are intensively studied for satisfying such requirements (see, for example, Chemical Reviews, 2007, 107, p. 1296-1323, and "Organic Field-Effect Transistors", 2007, CRC Press, p. 159-228).

Organic semiconductor materials are used as a photoelectric conversion material thereby obtaining organic photoelectric conversion devices such as optical sensors (see, for example, JP-A-2003-234460, JP-A-2003-332551, and JP-A-2005-268609 ("JP-A" means unexamined published Japanese patent application)), or organic thin-film solar cells (see, for example, "Organic Photovoltaics" (published in 2005, Taylor & Francis), p. 49-104, and Chemical Reviews, 2007, 107, p. 1324-1338). These organic photoelectric conversion devices are easier to produce as compared to the devices using inorganic semiconductor materials such as silicon. Especially, when an organic semiconductor material capable of performing film production according to a wet process is used, it is possible to manufacture large-scale devices at a low cost under a low temperature. There is ever reported, for example, the organic photoelectric conversion device using a photoelectric conversion layer that is a wet-process formed blend film composed of P3HT (poly (3-hexylthiophene)) and PCBM ([6,6]-phenyl-$C_{61}$-butyric acid methyl ester). However, the photoelectric conversion performance of the conventional organic photoelectric conversion device is inferior to that of a silicon photoelectric conversion device. Therefore, improvement in performance of the organic photoelectric conversion device is demanded. The most outstanding issue to improvement in performance is that especially a long wavelength range (near infrared range) has not been used in the current device using both P3HT and PCBM because of a narrow light absorption wavelength range of the materials that are used in the device. Resultantly, energy conversion efficiency is low for use of the solar cell, and sensitivity that is required for an optical sensor is not provided in the long wavelength range (near infrared range). For this reason, it is required to develop an organic photoelectric conversion material capable of absorbing light even in a longer wavelength range (near infrared range), and capable of providing photoelectric conversion performance (see, for example, "Organic Photovoltaics" (published in 2005, Taylor & Francis), p. 49-104, and Chemical Reviews, 2007, 107, p. 1324-1338).

As a material capable of absorbing light even in a near infrared range, croconium dyes are known (see, for example, JP-A-2001-117201, and Dyes and Pigments, 1988, 10, p. 13-22). However, there is no specific description in which the croconium dye is actually used in an organic photoelectric conversion device. Consequently, no photoelectric conversion performance is confirmed.

SUMMARY OF THE INVENTION

The present invention resides in an organic photoelectric conversion material for use in an organic thin-film photoelectric conversion device, which comprises a compound represented by formula 1:

Formula 1 wherein D represents an electron-donating aromatic substituent whose bonding site atom is a $sp^2$ carbon atom; and a plurality of D may be the same or different from each other.

Further, the present invention resides in an organic thin-film photoelectric conversion device, having two electrode layers and an organic thin-film photoelectric conversion layer, wherein the photoelectric conversion layer comprises the organic photoelectric conversion material comprising the compound represented by formula 1.

The inventor has found that it is possible to provide following specific photoelectric conversion materials and the following high-performance organic thin-layer photoelectric conversion device using the organic photoelectric conversion material.

According to the present invention, there is provided the following means:

(1) An organic photoelectric conversion material for use in an organic thin-film photoelectric conversion device, comprising a compound represented by formula 1:

Formula 1 wherein D represents an electron-donating aromatic substituent whose bonding site atom is a $sp^2$ carbon atom; and a plurality of D may be the same or different from each other.

(2) An organic thin-film photoelectric conversion device, having two electrode layers and an organic thin-film photoelectric conversion layer, wherein the photoelectric conversion layer comprises the organic photoelectric conversion material as described in (1).

(3) The organic thin-film photoelectric conversion device as described in (2), wherein the photoelectric conversion layer comprises an n-type organic semiconductor material in addition to the organic photoelectric conversion material.

(4) The organic thin-film photoelectric conversion device as described in (3), wherein the photoelectric conversion layer has a blend film comprising both the organic photoelectric conversion material and the n-type organic semiconductor material.

(5) The organic thin-film photoelectric conversion device as described in (3) or (4), wherein the n-type organic semiconductor material is at least one compound selected from the group consisting of a fullerene compound, a phthalocyanine compound, a naphthalene tetracarbonyl compound, and a perylene tetracarbonyl compound.

(6) The organic thin-film photoelectric conversion device as described in any one of (3) to (5), wherein the n-type organic semiconductor material is a fullerene compound.

(7) The organic thin-film photoelectric conversion device as described in any one of (2) to (6), wherein a film of the photoelectric conversion layer is formed by a solution-coating method.

(8) The organic thin-film photoelectric conversion device as described in (7), wherein a solvent in the solution-coating method contains at least one solvent having a boiling point of 135° C. or more and less than 300° C.

(9) The organic thin-film photoelectric conversion device as described in any one of (2) to (8), further having a buffer layer containing an electrically conductive polymer, the buffer layer being disposed between at least one of the electrode layers and the organic photoelectric conversion layer.

(10) The organic thin-film photoelectric conversion device as described in any one of (2) to (9), which is sealed under an inert atmosphere after production of the organic thin-film photoelectric conversion device.

According to the present invention, it is possible to obtain an organic photoelectric conversion material capable of forming a film by using a coating method, and capable of providing a good photoelectric conversion performance even in a long wavelength range (near infrared range). Further, a high-performance organic thin-film photoelectric conversion device with sensitivity in the near infrared range may be obtained by using the organic photoelectric conversion material.

Other and further features and advantages of the invention will appear more fully from the following description, appropriately referring to the accompanying drawings.

DETAILED DESCRIPTION OF THE INVENTION

The compound represented by formula 1 that is used in the present invention is described in detail. Hereinafter the compound represented by formula 1 may also be referred to as the organic photoelectric conversion material of the present invention in some cases.

Formula 1 wherein D represents an electron-donating aromatic substituent whose bonding site atom is a sp² carbon atom. The electron-donating aromatic substituent is defined as an aromatic compound whose electron density is denser than that of the non-substituted benzene ring, and also as the aromatic compound that is more easily oxidized, but more hardly reduced as compared to benzene. A plurality of D may be the same or different from each other. From viewpoints of both photoelectric conversion performance and solubility, the structure represented by D has preferably 3 to 30 carbon atoms, and more preferably 6 to 20 carbon atoms. D is preferably represented by any one of the following formulae D-1 to D-11.

D-1

D-2

D-3

D-4

D-5

D-6

D-7

D-8

-continued

In the above chemical formulae, the mark "*" indicates a bonding site.

In D-1 to D-11, A represents $CR_2$, O, S, Se, Te, or NR. B represents CR, or N. R represents a hydrogen atom, or a substituent. m represents an integer. A plurality of R may be the same or different from each other. The substituent represented by D is not particularly limited, and may be selected from W that is described below. The substituent is preferably a halogen atom, an alkyl group, an aryl group, a heterocyclic group, a hydroxyl group, a nitro group, or an amino group. A plurality of R may bond together to form a ring. Such the embodiment is also preferable.

Among D-1 to D-11, D-1 to D-7 are furthermore preferable. D-1, D-2, D-3, D-4, and D-6 are especially preferable.

In the present invention, when specific moiety in the substituent is called "group", the site itself may not be substituted or may be substituted by one or more (to a possible maximum number) substituents. For example, "an alkyl group" means a substituted or unsubstituted alkyl group. Namely, the substituents which can be used in the compound for use in the present invention can be further substituted.

When such a substituent is set "W", the substituent represented by W may be any substituent and is not particularly limited, and, examples thereof include a halogen atom, an alkyl group (including, as well as a linear or branched alkyl group, a cycloalkyl group, a bicycloalkyl group, and a tricycloalkyl group,), an alkenyl group (including, as well as a linear or branched alkenyl group, a cycloalkenyl group and a bicycloalkenyl group), an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group, a boronic acid group ($-B(OH)_2$), a phosphate group ($-OPO(OH)_2$), a sulfate group ($-OSO_3H$), and other known substituents.

Specifically, the substituent represented by W represents the group as shown in the following items (1) to (48).
(1) Halogen atom (e.g., a fluorine atom, a chlorine atom, a bromine atom, an iodine atom)
(2) Alkyl group (which means a linear, branched or cyclic substituted or unsubstituted alkyl group, and examples of the alkyl group include the groups as shown in the following items (2-a) to (2-e))
(2-a) Alkyl group (alkyl group having preferably from 1 to 30, more preferably from 1 to 20, carbon atoms, e.g., methyl, ethyl, n-propyl, isopropyl, tert-butyl, n-octyl, eicosyl, 2-chloroethyl, 2-cyanoethyl, 2-ethylhexyl)
(2-b) Cycloalkyl group (preferably a substituted or unsubstituted cycloalkyl group having from 3 to 30, more preferably from 3 to 20, carbon atoms, e.g., cyclohexyl, cyclopentyl, 4-n-dodecyl-cyclohexyl)
(2-c) Bicycloalkyl group (preferably a substituted or unsubstituted bicycloalkyl group having from 5 to 30, more preferably from 5 to 20, carbon atoms, e.g., bicyclo[1,2,2]heptan-2-yl, bicyclo[2,2,2]octan-3-yl)
(2-d) Tricycloalkyl group (preferably a substituted or unsubstituted tricycloalkyl group having from 7 to 30, more preferably from 7 to 20, carbon atoms, e.g., 1-adamantyl)
(2-e) Polycycloalkyl group having 4 or more cyclic structures
The alkyl group in the substituents described below (for example, an alkyl group in an alkylthio group) means an alkyl group having such a concept and further includes an alkenyl group and an alkynyl group.
(3) Alkenyl group (which means a linear, branched or cyclic substituted or unsubstituted alkenyl group, and examples of the alkenyl group include the groups as shown in the following items (3-a) to (3-c))
(3-a) Alkenyl group (preferably a substituted or unsubstituted alkenyl group having from 2 to 30, more preferably from 2 to 20, carbon atoms, e.g., vinyl, allyl, prenyl, geranyl, oreyl)
(3-b) Cycloalkenyl group (preferably a substituted or unsubstituted cycloalkenyl group having from 3 to 30, more preferably from 3 to 20, carbon atoms, e.g., 2-cyclopenten-1-yl, 2-cyclohexen-1-yl)
(3-c) Bicycloalkenyl group (a substituted or unsubstituted bicycloalkenyl group, preferably a substituted or unsubstituted bicycloalkenyl group having from 5 to 30, more preferably from 5 to 20, carbon atoms, e.g., bicyclo[2,2,1]hept-2-en-1-yl, bicyclo[2,2,2]oct-2-en-4-yl)
(4) Alkynyl group (preferably a substituted or unsubstituted alkynyl group having from 2 to 30, more preferably from 2 to 20, carbon atoms, e.g., ethynyl, propargyl, trimethylsilylethynyl)
(5) Aryl group (preferably a substituted or unsubstituted aryl group having from 6 to 30, more preferably from 6 to 20, carbon atoms, e.g., phenyl, p-tolyl, naphthyl, m-chlorophenyl, o-hexadecanoylaminophenyl, ferrocenyl)
(6) Heterocyclic group (preferably a monovalent group resultant from removing one hydrogen atom of a 5- or 6-membered substituted or unsubstituted aromatic or non-aromatic heterocyclic compound, more preferably a 5- or 6-membered aromatic heterocyclic group having from 2 to 50 carbon atoms, and their hetero atoms of thereof include N, O, Se, Te, Si and Ge; e.g., 2-furyl, 2-thienyl, 2-pyrimidinyl, 2-benzothiazolyl; the heterocyclic group may also be a cationic heterocyclic group such as 1-methyl-2-pyridinio and 1-methyl-2-quinolinio)
(7) Cyano group
(8) Hydroxyl group
(9) Nitro group
(10) Carboxyl group (11) Alkoxy group (preferably a substituted or unsubstituted alkoxy group having from 1 to 30, more preferably from 1 to 20, carbon atoms, e.g., methoxy, ethoxy, isopropoxy, tert-butoxy, n-octyloxy, 2-methoxyethoxy)

(12) Aryloxy group (preferably a substituted or unsubstituted aryloxy group having from 6 to 30, more preferably from 6 to 20, carbon atoms, e.g., phenoxy, 2-methylphenoxy, 4-tert-butylphenoxy, 3-nitrophenoxy, 2-tradecanoylaminophenoxy)

(13) Silyloxy group (preferably a silyloxy group having from 3 to 30, more preferably from 2 to 20, carbon atoms, e.g., trimethylsilyloxy, tert-butyldimethylsilyloxy)

(14) Heterocyclic oxy group (preferably a substituted or unsubstituted heterocyclic oxy group having from 2 to 30, more preferably from 2 to 20, carbon atoms, e.g., 1-phenyltetrazol-5-oxy, 2-tetrahydropyranyloxy)

(15) Acyloxy group (preferably a formyloxy group, a substituted or unsubstituted alkylcarbonyloxy group having from 2 to 30, more preferably from 2 to 20, carbon atoms or a substituted or unsubstituted arylcarbonyloxy group having from 6 to 30, more preferably from 6 to 20, carbon atoms, e.g., formyloxy, acetyloxy, pivaloyloxy, stearoyloxy, benzoyloxy, p-methoxyphenylcarbonyloxy)

(16) Carbamoyloxy group (preferably a substituted or unsubstituted carbamoyloxy group having from 1 to 30, more preferably from 1 to 20, carbon atoms, e.g., N,N-dimethylcarbamoyloxy, N,N-diethylcarbamoyloxy, morpholinocarbonyloxy, N,N-di-n-octylaminocarbonyloxy, N-n-octylcarbamoyloxy)

(17) Alkoxycarbonyloxy group (preferably a substituted or unsubstituted alkoxycarbonyloxy group having from 2 to 30, more preferably from 2 to 20, carbon atoms, e.g., methoxycarbonyloxy, ethoxycarbonyloxy, tert-butoxycarbonyloxy, n-octylcarbonyloxy)

(18) Aryloxycarbonyloxy group (preferably a substituted or unsubstituted aryloxycarbonyloxy group having from 7 to 30, more preferably from 7 to 20, carbon atoms, e.g., phenoxycarbonyloxy, p-methoxyphenoxycarbonyloxy, p-n-hexadecyloxyphenoxycarbonyloxy)

(19) Amino group (preferably an amino group, a substituted or unsubstituted alkylamino group having from 1 to 30, more preferably from 1 to 20, carbon atoms or a substituted or unsubstituted anilino group having from 6 to 30 carbon atoms, e.g., amino, methylamino, dimethylamino, anilino, N-methyl-anilino, diphenylamino)

(20) Ammonio group (preferably an ammonio group or an ammonio group substituted by a substituted or unsubstituted alkyl, aryl or heterocyclic group having from 1 to 30, more preferably from 1 to 20, carbon atoms, e.g., trimethylammonio, triethylammonio, diphenylmethylammonio)

(21) Acylamino group (preferably a formylamino group, a substituted or unsubstituted alkylcarbonylamino group having from 1 to 30, more preferably from 1 to 20, carbon atoms or a substituted or unsubstituted arylcarbonylamino group having from 6 to 30 carbon atoms, e.g., formylamino, acetylamino, pivaloylamino, lauroylamino, benzoylamino, 3,4,5-tri-n-octyloxyphenylcarbonylamino)

(22) Aminocarbonylamino group (preferably a substituted or unsubstituted aminocarbonylamino group having from 1 to 30, more preferably from 1 to 20, carbon atoms, e.g., carbamoylamino, N,N-dimethylaminocarbonylamino, N,N-diethylaminocarbonylamino, morpholinocarbonylamino)

(23) Alkoxycarbonylamino group (preferably a substituted or unsubstituted alkoxycarbonylamino group having from 2 to 30, more preferably from 2 to 20, carbon atoms, e.g., methoxycarbonylamino, ethoxycarbonylamino, tert-butoxycarbonylamino, n-octadecyloxycarbonylamino, N-methyl-methoxycarbonylamino)

(24) Aryloxycarbonylamino group (preferably a substituted or unsubstituted aryloxycarbonylamino group having from 7 to 30, more preferably from 7 to 20, carbon atoms, e.g., phenoxycarbonylamino, p-chlorophenoxycarbonylamino, m-(n-octyloxy) phenoxycarbonylamino)

(25) Sulfamoylamino group (preferably a substituted or unsubstituted sulfamoylamino group having from 0 to 30, more preferably from 0 to 20, carbon atoms, e.g., sulfamoylamino, N,N-dimethylaminosulfonylamino, N-n-octylaminosulfonylamino)

(26) Alkyl- or aryl-sulfonylamino group (preferably a substituted or unsubstituted alkylsulfonylamino group having from 1 to 30, more preferably from 1 to 20, carbon atoms or a substituted or unsubstituted arylsulfonylamino group having from 6 to 30 carbon atoms, e.g., methylsulfonylamino, butylsulfonylamino, phenylsulfonylamino, 2,3,5-trichlorophenylsulfonylamino, p-methylphenylsulfonylamino)

(27) Mercapto group (28) Alkylthio group (preferably a substituted or unsubstituted alkylthio group having from 1 to 30, more preferably from 1 to 20, carbon atoms, e.g., methylthio, ethylthio, n-hexadecylthio)

(29) Arylthio group (preferably a substituted or unsubstituted arylthio group having from 6 to 30, more preferably from 6 to 20, carbon atoms, e.g., phenylthio, p-chlorophenylthio, m-methoxyphenylthio)

(30) Heterocyclic thio group (preferably a substituted or unsubstituted heterocyclic thio group having from 2 to 30, more preferably from 2 to 20, carbon atoms, e.g., 2-benzothiazolylthio, 1-phenyltetrazol-5-ylthio)

(31) Sulfamoyl group (preferably a substituted or unsubstituted sulfamoyl group having from 0 to 30, more preferably from 0 to 20, carbon atoms, e.g., N-ethylsulfamoyl, N-(3-dodecyloxypropyl)sulfamoyl, N,N-dimethylsulfamoyl, N-acetylsulfamoyl, N-benzoylsulfamoyl, N—(N'-phenylcarbamoyl)sulfamoyl)

(32) Sulfo group (33) Alkyl- or aryl-sulfinyl group (preferably a substituted or unsubstituted alkylsulfinyl group having from 1 to 30, more preferably from 1 to 20, carbon atoms or a substituted or unsubstituted arylsulfinyl group having from 6 to 30, more preferably from 61 to 20, carbon atoms, e.g., methylsulfinyl, ethylsulfinyl, phenylsulfinyl, p-methylphenylsulfinyl)

(34) Alkyl- or aryl-sulfonyl group (preferably a substituted or unsubstituted alkylsulfonyl group having from 1 to 30, more preferably from 1 to 20, carbon atoms or a substituted or unsubstituted arylsulfonyl group having from 6 to 30, more preferably from 6 to 20, carbon atoms, e.g., methylsulfonyl, ethylsulfonyl, phenylsulfonyl, p-methylphenylsulfonyl)

(35) Acyl group (preferably a formyl group, a substituted or unsubstituted alkylcarbonyl group having from 2 to 30, more preferably from 2 to 20, carbon atoms, a substituted or unsubstituted arylcarbonyl group having from 7 to 30, more preferably from 7 to 20, carbon atoms or a substituted or unsubstituted heterocyclic carbonyl group having from 4 to 30, more preferably from 4 to 20, carbon atoms and being bonded to a carbonyl group through a carbon atom, e.g., acetyl, pivaloyl, 2-chloroacetyl, stearoyl, benzoyl, p-n-octyloxyphenylcarbonyl, 2-pyridylcarbonyl, 2-furylcarbonyl)

(36) Aryloxycarbonyl group (preferably a substituted or unsubstituted aryloxycarbonyl group having from 7 to 30, more preferably from 7 to 20, carbon atoms, e.g., phenoxycarbonyl, o-chlorophenoxycarbonyl, m-nitrophenoxycarbonyl, p-tert-butylphenoxycarbonyl)
(37) Alkoxycarbonyl group (preferably a substituted or unsubstituted alkoxycarbonyl group having from 2 to 30, more preferably from 2 to 20, carbon atoms, e.g., methoxycarbonyl, ethoxycarbonyl, tert-butoxycarbonyl, n-octadecyloxycarbonyl)
(38) Carbamoyl group (preferably a substituted or unsubstituted carbamoyl group having from 1 to 30, more preferably from 1 to 20, carbon atoms, e.g., carbamoyl, N-methylcarbamoyl, N,N-dimethylcarbamoyl, N,N-di-n-octylcarbamoyl, N-(methylsulfonyl)-carbamoyl)
(39) Aryl- or heterocyclic-azo group (preferably a substituted or unsubstituted arylazo group having from 6 to 30, more preferably from 6 to 20, carbon atoms or a substituted or unsubstituted heterocyclic-azo group having from 2 to 30 carbon atoms, e.g., phenylazo, p-chlorophenylazo, 5-ethylthio-1,3,4-thiadiazol-2-ylazo)
(40) Imido group (preferably N-succinimido, N-phthalimido)
(41) Phosphino group (preferably a substituted or unsubstituted phosphino group having from 2 to 30, more preferably from 2 to 20, carbon atoms, e.g., dimethylphosphino, diphenylphosphino, methylphenoxyphosphino)
(42) Phosphinyl group (preferably a substituted or unsubstituted phosphinyl group having from 2 to 30, more preferably from 2 to 20, carbon atoms, e.g., phosphinyl, dioctyloxyphosphinyl, diethoxyphosphinyl)
(43) Phosphinyloxy group (preferably a substituted or unsubstituted phosphinyloxy group having from 2 to 30, more preferably from 2 to 20, carbon atoms, e.g., diphenoxyphosphinyloxy, dioctyloxyphosphinyloxy)
(44) Phosphinylamino group (preferably a substituted or unsubstituted phosphinylamino group having from 2 to 30, more preferably from 2 to 20, carbon atoms, e.g., dimethoxyphosphinylamino, dimethylaminophosphinylamino)
(45) Phospho group
(46) Silyl group (preferably a substituted or unsubstituted silyl group having from 3 to 30, more preferably from 3 to 20, carbon atoms, e.g., trimethylsilyl, triethylsilyl, tri(isopropyl)silyl, tert-butyldimethylsilyl, phenyldimethylsilyl)
(47) Hydrazino group (preferably a substituted or unsubstituted hydrazino group having from 0 to 30, more preferably from 0 to 20, carbon atoms, e.g., trimethylhydrazino)
(48) Ureido group (preferably a substituted or unsubstituted ureido group having from 0 to 30, more preferably from 3 to 20, carbon atoms, e.g., N,N-dimethylureido)

The two substituents represented by W may also have a structure condensed with a ring, e.g., an aromatic or non-aromatic hydrocarbon ring, a heterocyclic ring or a polycyclic condensed ring formed by the combination of these rings, e.g., a benzene ring, a naphthalene ring, an anthracene ring, a phenanthrene ring, fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, a indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring, a phenazine ring. Among these, a benzene ring, a pyrrole ring, a furan ring, a thiophene ring, an imidazole ring, an oxazole ring, a thiazole ring, a pyridine ring, and a pyrazine ring are preferable.

Among these substituents W, those having a hydrogen atom may be deprived of the hydrogen atom and substituted by the above-described substituent. Examples of these substituents include —CONHSO$_2$— group (sulfonylcarbamoyl group, carbonylsulfamoyl group), —CONHCO— group (carbonylcarbamoyl group), and —SO$_2$NHSO$_2$— group (sulfonylsulfamoyl group). Specific examples thereof include an alkylcarbonylaminosulfonyl group (e.g., acetylaminosulfonyl group), an arylcarbonylaminosulfonyl group (e.g., benzoylaminosulfonyl group), an alkylsulfonylaminocarbonyl group (e.g., methylsulfonylaminocarbonyl group), and an arylsulfonylaminocarbonyl group (e.g., p-methylphenylsulfonylaminocarbonyl group).

The compounds represented by formula 1, those in which two D's are the same are especially preferable.

Specific examples of the organic photoelectric conversion material represented by formula 1 of the present invention are shown in the followings, but the present invention is not limited thereto. (Et represents an ethyl group and Ph represents a phenyl group in the following chemical formulae.).

Exemplifed compound 1

Exemplifed compound 2

Exemplifed compound 3

Exemplifed compound 4

Exemplifed compound 5

Exemplifed compound 6
Exemplifed compound 7
Exemplifed compound 8
Exemplifed compound 9
Exemplifed compound 10
Exemplifed compound 11
Exemplifed compound 12
Exemplifed compound 13

Exemplifed compound 14
Exemplifed compound 15
Exemplifed compound 16
Exemplifed compound 17
Exemplifed compound 18
Exemplifed compound 19

Exemplifed compound 20

Exemplifed compound 21

Exemplifed compound 22

Exemplifed compound 23

Exemplifed compound 24

Exemplifed compound 25

Exemplifed compound 26

Exemplifed compound 27

Exemplifed compound 28

Exemplifed compound 29

Exemplifed compound 30

Exemplifed compound 31

Exemplifed compound 32

Exemplifed compound 33

Exemplifed compound 34

Exemplifed compound 35

Exemplifed compound 36

Exemplifed compound 37

Exemplifed compound 38

The above-described exemplified compounds may be synthesized in accordance with methods described in, for example, Dyes and Pigments, 1988, 10, p. 12-22, or JP-A No. 2001-117201.

It is noted that the organic photoelectric conversion material of the present invention that is represented by formula 1 may be described by formula 1' in which the site of electrons are shifted from the formula 1. In formula 1', each of D' and D" has the same meanings as D in formula 1, except that a plus (+) charge is present in the structure represented by D".

Formula 1'

According to the chemical notation of the formula 1', for example, the exemplified compound 1 is described below.

Exemplified compound 1

The organic photoelectric conversion material of the present invention is easy to form a good quality thin film, and therefore the material is suitably used for forming a thin film. When a thin film is formed, it is preferable that the organic photoelectric conversion material of the present invention is mixed with a binder material, another organic semiconductor material or the like whereby they are used as a film containing them. In this embodiment, the compound represented by the formula 1 is preferably contained in the film in an amount of equal to or more than 1% by mass, more preferably equal to or more than 5% by mass, and furthermore preferably equal to or more than 10% by mass, relative to the film respectively. The thickness of the photoelectric conversion layer is not particularly limited, but it is preferably 1 nm to 1 μm, and more preferably 5 nm to 500 nm.

As a method of forming a thin film containing the organic photoelectric conversion material of the present invention, there can be used any of a dry film forming process and a wet film forming process. The wet film forming process is preferable. Specific examples of the dry film forming process include a physical vapor phase growth method such as a vacuum evaporation method, a spattering method, an ion plating method and a molecular beam epitaxy (MBE) method, and a chemical vapor deposition (CVD) method such as a plasma polymerization. As the wet film forming process (solution-coating method), there is a method of dissolving an organic photoelectric conversion material in a solvent capable of dissolving the material or dispersing the material homogeneously, and making the resultant solution or dispersion a thin coating to form a film. As specific examples, there can be used methods such as a cast process, a blade coating process, a wire bar coating process, a splay coating process, a dip (an immersion) coating process, a bead coating process, an air knife coating process, a curtain coating process, an ink jet coating process, a spin coating process, and a Langmuir-Blodgett (LB) process. Preferably there can be used a cast process, a spin coating process and an ink jet coating process. More preferably there can be used a spin coating process In the case of forming an organic photoelectric conversion layer by the wet film forming process, a coating solution is prepared by dissolving or dispersing the organic photoelectric conversion material solely or the material and a binder in an appropriate organic solvent (e.g., a hydrocarbon solvent, such as hexane, octane, decane, toluene, xylene, ethylbenzene, 1-methylnaphthalene or 1,2-dichlorobenzene; a ketone solvent, such as acetone, methyl ethyl ketone, methyl isobutyl ketone or cyclohexanone; a halogenated hydrocarbon solvent, such as dichloromethane, chloroform, tetrachloromethane, dichloroethane, trichloroethane, tetrachloroethane, chlorobenzene, dichlorobenzene or chlorotoluene; an ester solvent, such as ethyl acetate, butyl acetate or amyl acetate; an alcohol solvent, such as methanol, propanol, butanol, pentanol, hexanol, cyclohexanol, methyl cellosolve, ethyl cellosolve or ethylene glycol; an ether solvent, such as dibutyl ether, tetrahydrofuran, dioxane or anisole; a polar solvent, such as N,N-dimethylformamide, N,N-dimethylacetamide, 1-methyl-2-pyrrolidone, 1-methyl-2-imidazolidinone or dimethyl sulfoxide) and/or water, and the coating solution prepared can be formed into thin film by various coating methods.

The solvent is not particularly limited. However, containing of a high boiling point solvent in the solvent is preferable on account that volatilization rate slows and also molecular arrangement order in the film formed by using the solvent becomes better. It is preferable that a solvent having a high boiling point of 135° C. or more and less than 300° C. (more preferably from 135° C. to 210° C.) is contained in a solvent in an amount of 1% by mass to 100% by mass of the total solvent. Examples of the high boiling point solvent include ethyl cellosolve (boiling point (b.p.): 135° C.), n-amyl alcohol (b.p.: 137° C.), xylene (b.p.: 140° C.), amyl acetate (b.p.: 142° C.), β-picoline (b.p.: 143° C.), 1,1,2,2-tetrachloroethane (b.p.: 146° C.), N,N-dimethylformamide (b.p.: 153° C.), 1-hexanol (b.p.: 157° C.), o-chlorotoluene (b.p.: 159° C.), petachloroethane (b.p.: 162° C.), N,N-dimethylacetoamide (b.p.: 165° C.), o-dichlorobenzene (b.p.: 180° C.), dimethylsulfoxide (b.p.: 189° C.), ethyleneglycol (b.p.: 198° C.), 1-methyl-2-pyrolidone (b.p.: 202° C.), nitrobenzene (b.p.: 211° C.), 1,2,4-trichlorobenzene (b.p.: 214° C.), quinoline (b.p.: 238° C.), and 1-chloronaphthalene (b.p.: 260° C.). Among these solvents, xylene, β-picoline, o-chlorotoluene, or o-dichlorobenzene is especially preferable. The concentration of the organic photoelectric conversion material of the present invention in such a coating solution is adjusted to a range of preferably 0.1 to 80 mass %, more preferably 0.1 to 30 mass %, and further preferably 0.1 to 10 mass %, and thereby the film can be formed with an arbitrary thickness.

In the case where a resin binder is used in the present invention, examples of the resin binder include insulating polymers such as polystylene, polycarbonate, polyarylate, polyester, polyamide, polyimide, polyurethane, polysiloxane, polysulfone, polymethylmethacrylate, polymethylacrylate, cellulose, polyethylene and polypropylene; and copolymers of these polymers; photoconductive polymers such as polyvinylcarbazol and polysilane, and electrically conductive polymers such as polythiophen, polypyrrole, polyaniline, and polypara phenylenevinilene. The resin binder may be used solely or, alternatively two or more kinds of the resin binder may be used in combination. Taking a mechanical strength of the thin-film into consideration, preferred are resin binders having a high glass transition temperature. Whereas, taking a charge transfer degree into consideration, preferred are resin binders containing no polar group, photoconductive polymers and electrically conductive polymers. It is preferable in characteristics not to use such the resin binder. But, the resin binder is sometimes used according to the purpose. In this case, an amount of the resin binder used is not particularly limited, but preferably the binder is used in the range of from 0.1 to 90% by mass, more preferably in the range of from 0.1 to 50% by mass, and further preferably in the range of from 0.1 to 30% by mass, based on the organic photoelectric conversion layer.

At the time of film formation, the substrate may be heated or cooled. By changing the substrate temperature, it becomes possible to control morphology and molecular orientational states of the film. The substrate temperature, though not particularly limited, is preferably between 0° C. and 200° C.

The composition of the organic thin-film photoelectric conversion device of the present invention is explained in detail below.

Figure 1:
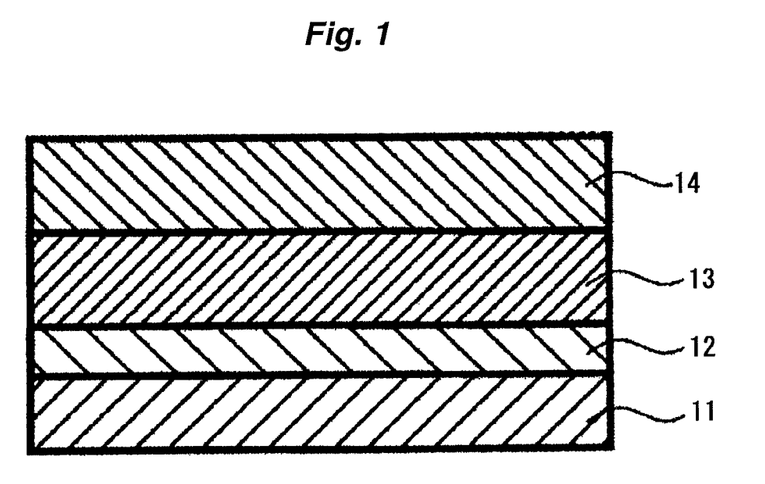
FIG. 1 is a cross-sectional view schematically showing a structure of an embodiment of the organic thin-film photoelectric conversion device of the present invention.

FIG. 1 is a cross-sectional view schematically showing one of preferable embodiments of the organic thin-film photoelectric conversion device of the present invention. The device of FIG. 1 has a multi-layer structure in which a substrate 11 is disposed as the lowest layer, and an electrode layer 12, a photoelectric conversion layer 13 containing the photoelectric conversion material of the present invention, and an electrode layer 14 are disposed above the substrate in this order. Between the electrode layer 12, or 14 and the photoelectric conversion layer 13, there may be disposed additional layers such as a buffer layer capable of enhancing smoothness of the surface, a carrier injecting layer capable of accelerating injection of holes or electrons from the electrode, a carrier transporting layer capable of transporting holes or electrons, or a carrier block layer capable of blocking holes or electrons, each of which is not described in FIG. 1. Among these layers, one layer may be also used as other layers. In the present invention, these layers that are disposed between the electrode layer and the photoelectric conversion layer are all described as a buffer layer irrespective of their functions. Further, the electrode layer and other layers are not necessarily flat, but may have a large irregularity, or a three dimensional shape (for example, comb shape).

The material for use in the substrate 11 is not particularly limited, as long as the material transmits a visible light, or an infrared light. Transmittance of visible light, or infrared light is preferably equal to or more than 60%, more preferably equal to or more than 80%, and most preferably equal to or more than 90%. Examples of the material include polyester films such as polyethylene naphtalate (PEN), or polyethylene terephthalate (PET), polyimide films, ceramic, silicon, quartz, and glass. The thickness of the substrate is not particularly limited.

As to materials usable for the electrode layer 12, there is no particular restriction so long as they are pervious to visible or infrared light and show conductivity. The visible or infrared transmittance of the material used is preferably at least 60%, far preferably at least 80%, particularly preferably at least 90%. Suitable examples of such a material include transparent conductive oxides, such as ITO, IZO, $SnO_2$, ATO (antimony-doped tin oxide), ZnO, AZO (Al-doped zinc oxide), GZO (gallium-doped zinc oxide), $TiO_2$ and FTO (fluorine-doped tin oxide). Of these oxides, ITO and IZO are especially preferred from the viewpoints of process suitability and smoothness. The thickness is not particularly limited, but it is preferably 1 nm to 200 nm, and more preferably 5 nm to 100 nm. When the electrode layer 12 has a structural independency, the substrate 11 is not necessary. When the electrode layer 12 is also used as a substrate 11, the film thickness of the electrode layer may be thicker than that described above.

The photoelectric conversion layer 13 contains the organic photoelectric conversion material of the present invention. The photoelectric conversion layer may be a single layer consisting of the organic photoelectric conversion material of the present invention, or may have a multi-layer structure including a layer consisting of the organic photoelectric conversion material of the present invention and one or more other layers containing other semiconductor materials. The order and the number of the layers in the multi-layer structure are not particularly limited. Further, the photoelectric conversion layer may be a layer containing both the organic photoelectric conversion material of the present invention and other semiconductor materials. In this embodiment, both materials may be completely mixed in a molecular level, or may form any phase-separated structure. The other semiconductor materials used in these embodiments are preferably n-type semiconductor materials. It is most preferable to use a layer containing a blend film composed of the organic photoelectric conversion material of the present invention and other semiconductor materials as a photoelectric conversion layer.

The n-type semiconductor materials may be an organic semiconductor material, or an inorganic semiconductor material, as long as the semiconductor material has an electron transportation property. As the semiconductor materials, fullerene compounds, phthalocyanine compounds, naphthalene tetracarbonyl compounds, perylene tetracarbonyl compounds, or inorganic semiconductor materials are preferable. Further, fullerene compounds, phthalocyanine compounds, naphthalene tetracarbonyl compounds, and perylene tetracarbonyl compounds are more preferable. Especially, fullerene compounds are preferable. In the present invention, the fullerene compound is not particularly limited, as long as the compound has a fullerene structure in its molecule. Specifically, as the fullerene compound, any of $C_{60}$, $C_{70}$, $C_{76}$, $C_{78}$, $C_{80}$, $C_{82}$, $C_{84}$, $C_{86}$, $C_{88}$, $C_{90}$, $C_{96}$, $C_{116}$, $C_{180}$, $C_{240}$, $C_{540}$, or the like may be used. Among these compounds, a substituted or unsubstituted $C_{60}$, $C_{70}$, or $C_{86}$ is preferable. PCBM ([6,6]-phenyl-$C_{61}$-butyric acid methyl ester) and analogs thereof are especially preferable. Examples of the analog include the same compounds as the PCBM, which have $C_{70}$, $C_{86}$, or the like substituted for the portion of $C_{60}$; or other aromatic ring or a hetero ring substituted for the benzene ring substituent; or n-butyl ester, iso-butyl ester, or the like substituted for the methyl ester. Similar to the fullerene compound, the phthalocyanine compound is not particularly limited, as long as the compound has a phthalocyanine structure in its molecule. Specifically, the phthalocyanine compound is a substituted or unsubstituted phthalocyanine and analogs thereof. The phthalocyanine analogs include not only various kinds of metal phthalocyanine, but also tetrapyrazinophorpyrazine, naphthalocyanine and anthracyanine. As the phthalocyanine compounds, those having an electron-withdrawing group are preferable. Further, those substituted with a fluorine atom (for example, $F_{16}CuCp$, and FPc-1) are more preferable. Further, the naphthalene tetracarbonyl compound is not particularly limited, as long as the compound has a naphthalene tetracarboxylic acid structure in its molecule. As the naphthalene tetracarbonyl compound, naphthalene tetracarboxylic acid anhydride (NTCDA), naphthalene bisimide compound (NTCDI), and perinone dye (for example, Pigment Orange 43 (PO43), Pigment Red 194) are preferable. The perylene tetracarbonyl compound is not particularly limited, as long as the compound has a perylene tetracarboxylic acid structure in its molecule. As the perylene tetracarbonyl compound, perylene tetracarboxylic acid anhydride (PTCDA), perylene bisimide compound (PTCDI), and benzimidazole-condensed perylene compound (PV) are preferable. Especially preferable examples of the n-type semiconductor material are set forth below. Me represents an methyl group and R represents a hydrogen atom or a substituent (for example, a linear or branched substituted or unsubstituted alkyl group, and a substituted or unsubstituted phenyl group) in the following chemical formulae.

-continued

The n-type semiconductor material used in the present invention is added in an amount of preferably from 0% by mass to 1000% by mass, more preferably from 10% by mass to 500% by mass, and furthermore preferably from 20% by mass to 200% by mass, relative to 100% by mass of the compound represented by formula 1. A content of the compound represented by formula 1 is preferably from 1% by mass to 100% by mass, more preferably from 10% by mass to 100% by mass, and furthermore preferably from 20% by mass to 100% by mass in the photoelectric conversion film.

The material used in the buffer layer may be an organic material, or an inorganic material, as long as the material has a carrier transportation property. As the buffer layer material, amorphous materials are preferable. The buffer material having a hole transportation property is not particularly limited, but preferably electrically conductive polymers (for example, PEDOT:PSS), triarylamine compounds (for example, m-MTDATA), or inorganic semiconductor materials (for example, NiO) are preferable. Especially electrically conductive polymers are preferable. The buffer material having an electron transportation property is not particularly limited, but preferably not only those materials described as examples of n-type organic semiconductor materials, but also metal complex compounds (for example, Alq), bathocuproin, inorganic fluorides (for example, LiF), inorganic oxides (for example, $SiO_x$, $TiO_x$, ZnO), electrically conductive polymers (for example, polyparaphenylenevinylene having a cyano group (CN—PPV), or perinone polymers (BBL). Among these materials, naphthalene compounds, bathocuproin, inorganic fluorides, or inorganic oxides are more preferable.

As to materials usable for the electrode layer 14, there is no particular restriction so long as they show conductivity. From the viewpoint of enhancing the light utilization efficiency, highly reflective materials are preferably used. Of such materials, Al, Pt, W, Au, Ag, Ta, Cu, Cr, Mo, Ti, Ni, Pd and Zn are especially preferred; and Al, Pt, Au and Ag are most preferred. The thickness of the electrode layer 14 is not particularly limited, but it is preferably 1 nm to 1 μm, and more preferably 5 nm to 500 nm.

For enhancement of the storage stability of the device, it is preferable that the device is entirely sealed with a sealing material under an inactive atmosphere (for example, a nitrogen atmosphere) so that the device can be held in the inert atmosphere. Examples of the sealing material include inorganic materials such as metals, glass, silicon nitride, or alumina, and organic materials such as parylene. When the device is sealed, an agent such as a desiccant may be encapsulated.

The organic thin-layer photoelectric conversion device of the present invention may be used for energy conversion (thin-layer organic solar cell), or as an optical sensor (for example, solid-state image sensor). When used for energy conversion, the organic thin-layer photoelectric conversion of the present invention may be used alone, or alternatively may be used with other organic thin-layer photoelectric conversions in tandem. A method of using them in tandem is detailed in "Applied Physics Letters", 2004, 85, p. 5757-5759, which may be used for reference. The organic thin-layer photoelectric conversion device of the present invention is excellent in photoelectric conversion performance particularly in a near infrared range. Therefore, when the organic thin-layer photoelectric conversion device of the present invention is used in tandem with a conventional device (for example, a device using P3HT and PCBM) that is excellent in photoelectric conversion performance in a visible range, high-powered solar cells may be obtained.

When the organic thin-layer photoelectric conversion device of the present invention is used as an optical sensor, it is preferable that a bias is applied between the electrodes 12 and 14 to read a signal so that S/N ratio is improved. In this embodiment, it is preferable that the bias to be applied to a photoelectric conversion layer is in the range of $1.0 \times 10^5$ V/cm to $1.0 \times 10^7$ V/cm. Solid-state image sensors using organic thin-layer photoelectric conversion devices are detailed in, for example, JP-A-2003-234460, JP-A-2003-332551, and JP-A-2005-268609, each of which may be used for reference.

The present invention will be described in more detail based on the following examples, but the invention is not intended to be limited thereto.

In the following examples, exemplified compounds 1, 5, 9, 16 and 18 were synthesized in accordance with methods described in "Dyes and Pigments", 1988, 10, p. 12-22, and JP-A-2001-117201. PCBM was bought from Frontier Carbon Corporation. The comparison compound P3HT (regioregular, Mw~87000) was bought from Aldrich Corporation.

EXAMPLES

Example 1

A glass substrate (2.5 cm×2.5 cm) with a patterning of ITO electrode was washed in isopropyl alcohol using ultrasonic, and then dried. Thereafter, a UV ozone treatment was performed for 30 minutes in order to remove organic contaminants on the surface of ITO substrate. Subsequently, an aqueous solution containing PEDOT (poly (3,4-ethylenedioxythiophene))/PSS (polystyrene sulfonic acid) (Baytron P standard good) was spin coated on the ITO substrate at 4000 rpm for 60 seconds, and then dried at 120° C. for 10 minutes. Thereby, a 50 nm film-thick buffer layer was formed. The film thickness was measured using a film thickness meter by a stylus method (DEKTAK6M (trade name) manufactured by ULVAC, Inc.). Hereinafter, the same measuring method is applied to the film thickness. Subsequently, after dissolving 10 mg of the exemplified compound 1 and 10 mg of PCBM in 1 ml of 1,2-dichlorobenzene (HPLC grade) in a glove box (nitrogen atmosphere), ultrasonic was irradiated to the above mixture for 5 minutes, and then the resultant solution was spin coated at 1000 rpm on the previously formed buffer layer. Thereby, a 200 nm or less thick photoelectric conversion layer having an almost uniform thickness was formed. On the photoelectric conversion layer, aluminum was vacuum-deposited at degree of vacuum of $2 \times 10^{-4}$ Pa or less using a vacuum-deposition equipment (EBX-8C (trade name), manufactured by ULVAC, Inc) so that the thickness was 80 nm. Thereby, a metal electrode was formed. Finally, by sealing with a glass sealing can and an UV curing resin in a glove box (nitrogen atmosphere), an organic thin-layer photoelectric conversion device having an effective area of 0.04 $cm^2$ was obtained.

Figure 2:
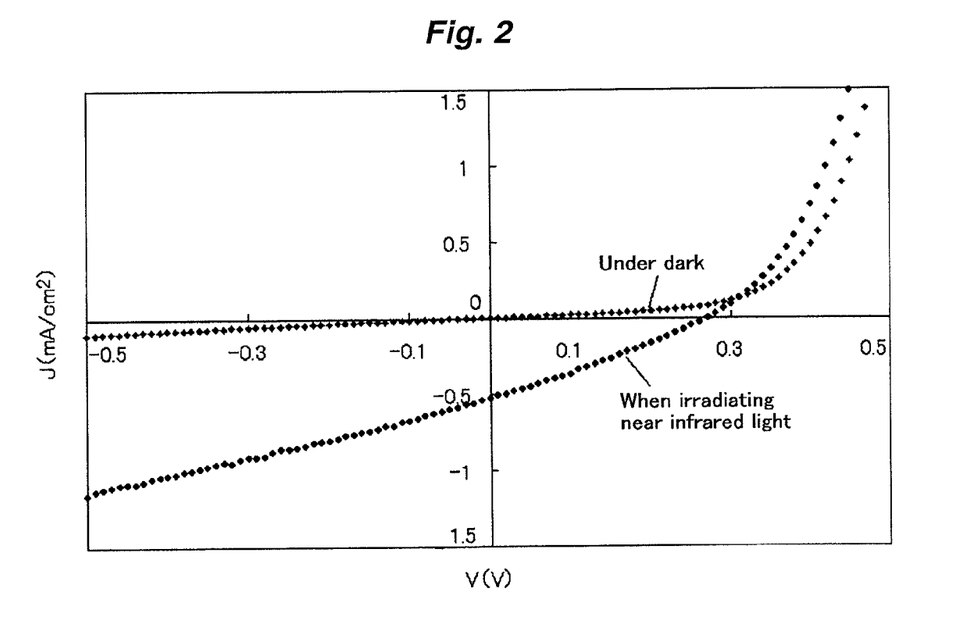
FIG. 2 is a graph showing current-voltage characteristics of the organic thin-layer photoelectric conversion device of the present invention using the exemplified compound 1, in two cases where the near infrared light is not irradiated and the near infrared light is irradiated.

To the thus-obtained device, was irradiated a light in which a light of a 700 nm or less wavelength range was cut through a cut-off filter (hereinafter, the light is called "a near infrared light"), while adjusting the amount of light to AM 1.5, 100 $mW/cm^2$ using both a solar simulator (150W scaled down type, manufactured by Oriel Corporation) and an air mass filter. Thereafter, current-voltage characteristics were measured using an electrochemical analyzer (ALS model 660B (trade name), manufactured by BAS Corporation). The results of measurement demonstrated excellent solar cell characteristics as shown in FIG. 2, namely short circuit-current (Jsc) of 0.52 $mA/cm^2$ and open voltage (Voc) of 0.28 V. From the results, it is understood that the organic thin-layer photoelectric conversion device using the exemplified compound 1 has a high sensitivity in a near infrared range whereby the device functions as a solar cell.

Figure 3:
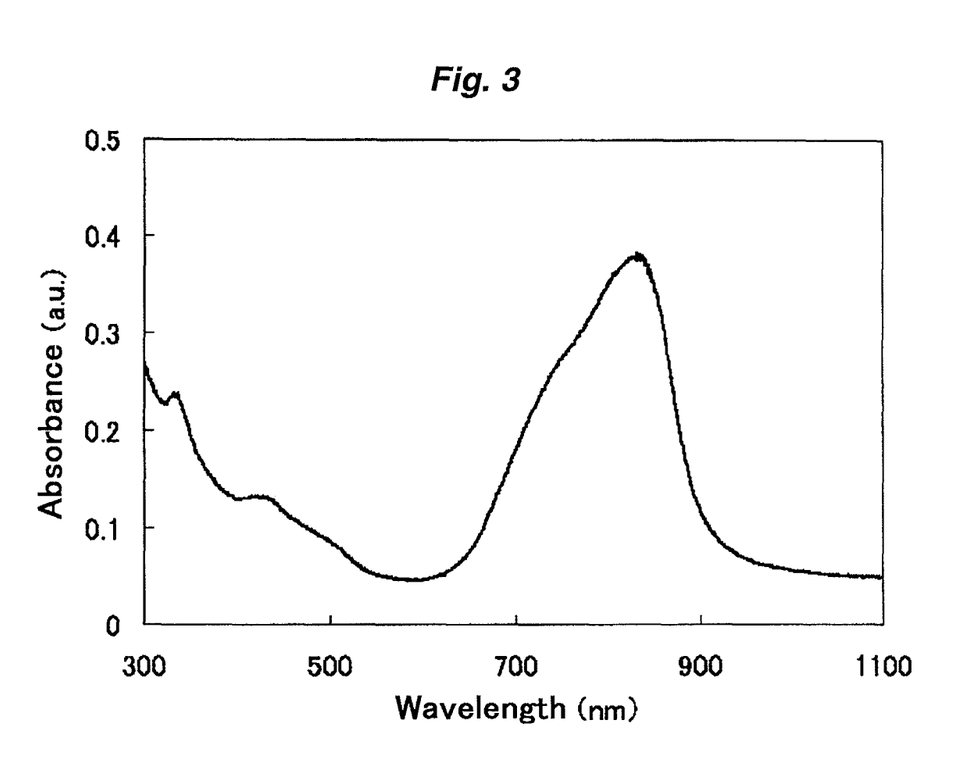
FIG. 3 is a graph showing an absorption spectrum of the organic thin-layer photoelectric conversion device in which the exemplified compound 1 is used.

In the same manner as the above except that a quartz substrate was used in place of the glass substrate with the patterning of ITO electrode, a photoelectric conversion film was spin coated on the PEDOT/PSS film. Then, an absorption spectrum was measured using an ultraviolet-visual-near infrared spectrophotometer (UV-3600 (trade name), manufactured by Shimadzu Corporation). As a result of measurement, a spectrum showing an absorption exhibiting an absorption maximum wavelength at 837 nm was obtained as shown in FIG. 3.

Example 2

Devices manufactured exactly in the same manner as Example 1 except that each of the exemplified compounds 5, 9, 16, and 18 was used in place of the exemplified compound 1 respectively exhibited high photoelectric conversion performance equivalent to the device of Example 1 at the near infrared range. The results of short circuit-current, open voltage, and absorption λ max of the photoelectric conversion layer of each of the devices are shown in Table 1.

Comparison Example 1

A comparison device was manufactured exactly in the same manner as Example 1 except that P3HT (poly (3-hexylthiophene)) was used in place of the exemplified compound 1. The thus-obtained device was evaluated exactly under the same conditions as Example 1. None of photoelectric conversion performance was exhibited to the near infrared light as shown in Table 1.

TABLE 1

| Compound | Short circuit-current | Open voltage | Absorption $\lambda_{max}$ | Remarks |
|---|---|---|---|---|
| Exemplified compound 1 | 0.52 $mA/cm^2$ | 0.28 V | 837 nm | This invention |
| Exemplified compound 5 | 0.40 $mA/cm^2$ | 0.27 V | 820 nm | This invention |
| Exemplified compound 9 | 0.37 $mA/cm^2$ | 0.28 V | 881 nm | This invention |
| Exemplified compound 16 | 0.42 $mA/cm^2$ | 0.30 V | 943 nm | This invention |
| Exemplified compound 18 | 0.33 $mA/cm^2$ | 0.26 V | 928 nm | This invention |
| P3HT | 0.00 $mA/cm^2$ | 0.00 V | 520 nm | Comparative example |

As is apparent from the above Examples and Comparison Example, it is understood that the organic photoelectric conversion material of the present invention has a high sensitivity at the near infrared light range, and the organic thin-layer photoelectric conversion device of the present invention exhibits a high photoelectric conversion performance to the near infrared light.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. § 119 (a) on Patent Application No. 2008-143256 filed in Japan on May 30, 2008, which is entirely herein incorporated by reference.

What I claim is:

1. An organic thin-film photoelectric conversion device, having two electrode layers and an organic thin-film photoelectric conversion layer, wherein the photoelectric conversion layer comprises (i) an organic photoelectric conversion material comprising a compound represented by formula 1:

Formula 1 wherein D represents an electron-donating aromatic substituent whose bonding site atom is a $sp^2$ carbon atom; and a plurality of D may be the same or different from each other, and (ii) an n-type organic semiconductor material.

2. The organic thin-film photoelectric conversion device according to claim 1, wherein the photoelectric conversion layer has a blend film comprising both the organic photoelectric conversion material and the n-type organic semiconductor material.

3. The organic thin-film photoelectric conversion device according to claim 1, wherein the n-type organic semiconductor material is at least one compound selected from the group consisting of a fullerene compound, a phthalocyanine compound, a naphthalene tetracarbonyl compound, and a perylene tetracarbonyl compound.

4. The organic thin-film photoelectric conversion device according to claim 1, wherein the n-type organic semiconductor material is a fullerene compound.

5. The organic thin-film photoelectric conversion device according to claim 1, wherein a film of the photoelectric conversion layer is formed by a solution-coating method.

6. The organic thin-film photoelectric conversion device according to claim 5, wherein a solvent in the solution-coating method contains at least one solvent having a boiling point of 135° C. or more and less than 300° C.

7. The organic thin-film photoelectric conversion device according to claim 1, further having a buffer layer containing an electrically conductive polymer, the buffer layer being disposed between at least one of the electrode layers and the organic photoelectric conversion layer.

8. The organic thin-film photoelectric conversion device according to claim 1, which is sealed under an inert atmosphere after production of the organic thin-film photoelectric conversion device.

9. The organic thin-film photoelectric conversion device according to claim 1, wherein the photoelectric conversion layer consists essentially of the organic photoelectric conversion material comprising the compound represented by formula 1 and the n-type organic semiconductor material.

10. The organic thin-film photoelectric conversion device according to claim 1, wherein D in formula 1 is represented by any one of the following formulae D-1 to D-11:

D-1

D-2

D-3

D-4

D-5

D-6

D-7

D-8

D-9

D-10

D-11 wherein the mark "*" indicates a bonding site; A represents $CR_2$, O, S, Se, Te, or NR; B represents CR or N; R represents a hydrogen atom or a substituent; m represents an integer; a plurality of R's may be the same or different from each other; and a plurality of R's may bond together to form a ring.

11. The organic thin-film photoelectric conversion device according to claim 1, wherein D in formula 1 is represented by any one of the following formulae D-1, D-2, D-3, D-4, and D-6:

D-1

D-2

D-3

D-4

D-6 wherein the mark "*" indicates a bonding site; A represents CR$_2$, O, S, Se, Te, or NR; B represents CR or N; R represents a hydrogen atom, or a substituent; m represents an integer; a plurality of R's may be the same or different from each other; and a plurality of R's may bond together to form a ring.

12. The organic thin-film photoelectric conversion device according to claim 1, wherein the compound represented by formula 1 is any one of exemplified compounds 1 to 38:

Exemplifed compound 15

Exemplifed compound 16

Exemplifed compound 17

Exemplifed compound 18

Exemplifed compound 19

Exemplifed compound 20

Exemplifed compound 21

Exemplifed compound 22

Exemplifed compound 23

Exemplifed compound 24

Exemplifed compound 25

Exemplifed compound 26

Exemplifed compound 27

Exemplifed compound 28

Exemplifed compound 29

Exemplifed compound 30

Exemplifed compound 31

Exemplifed compound 32

Exemplifed compound 33

Exemplifed compound 34

Exemplifed compound 35

Exemplifed compound 36

Exemplifed compound 37

Exemplifed compound 38

13. The organic thin-film photoelectric conversion device according to claim 1, wherein a thickness of the photoelectric conversion layer is 5 nm to 500 nm.

* * * * *